US006957651B2

(12) United States Patent
Nuckols et al.

(10) Patent No.: US 6,957,651 B2
(45) Date of Patent: Oct. 25, 2005

(54) SYSTEM FOR SIMULATING METABOLIC CONSUMPTION OF OXYGEN

(75) Inventors: Marshall L. Nuckols, Annapolis, MD (US); Kirk Vanzandt, Panama City, FL (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 830 days.

(21) Appl. No.: 10/051,731

(22) Filed: Jan. 22, 2002

(65) Prior Publication Data

US 2003/0138361 A1 Jul. 24, 2003

(51) Int. Cl.[7] .......... A61M 15/00
(52) U.S. Cl. .......... 128/200.24; 128/202.26; 128/204.22
(58) Field of Search .......... 128/200.24, 202.12, 128/202.21, 202.26, 204.22, 205.26

(56) References Cited

U.S. PATENT DOCUMENTS

| | | | | | |
|---|---|---|---|---|---|
| 4,265,238 | A * | 5/1981 | Swiatosz et al. | | 128/205.12 |
| 4,334,533 | A * | 6/1982 | Henkin | | 128/205.28 |
| 4,471,774 | A * | 9/1984 | Swiatosz | | 128/205.12 |
| 4,539,986 | A * | 9/1985 | Swiatosz et al. | | 128/205.13 |
| 4,796,467 | A * | 1/1989 | Burt et al. | | 73/168 |
| 5,029,578 | A * | 7/1991 | Swiatosz | | 128/202.26 |
| 5,647,345 | A * | 7/1997 | Saul | | 128/201.23 |
| 5,799,652 | A * | 9/1998 | Kotliar | | 128/205.11 |
| 5,848,589 | A * | 12/1998 | Welnetz | | 128/200.24 |
| 5,850,833 | A * | 12/1998 | Kotliar | | 128/202.12 |
| 6,009,870 | A * | 1/2000 | Tkatchouk | | 128/202.12 |
| 6,131,569 | A * | 10/2000 | Schuster | | 128/200.24 |
| 6,561,185 | B1 * | 5/2003 | Kroll | | 128/202.12 |
| 6,565,624 | B2 * | 5/2003 | Kutt et al. | | 95/8 |
| 6,820,619 | B2 * | 11/2004 | Kroll | | 128/205.11 |

* cited by examiner

*Primary Examiner*—Aaron J. Lewis
(74) *Attorney, Agent, or Firm*—James T. Shepherd

(57) ABSTRACT

A method and system are provided for simulating the metabolic consumption of oxygen contained in a breathable gas. A variable volume chamber cyclically increases/decreases in volume to receive the breathable gas/expel an exhaust gas. Hydrogen and carbon dioxide are introduced into the chamber to mix with the breathable gas to form the exhaust gas. Hydrogen is introduced in an amount sufficient to react with an amount of the oxygen in the exhaust gas equivalent to that used by a human during a selected level of activity. Carbon dioxide is introduced in an amount equivalent to that provided by a metabolic respiratory quotient associated with the same level of activity. A catalyst, exposed to the exhaust gas, causes a reaction between the hydrogen and oxygen in the exhaust gas to generate simulated human exhalation.

18 Claims, 1 Drawing Sheet

SYSTEM FOR SIMULATING METABOLIC CONSUMPTION OF OXYGEN

ORIGIN OF THE INVENTION

The invention described herein was made in the performance of official duties by employees of the Department of the Navy and may be manufactured, used, licensed by or for the Government for any governmental purpose without payment of any royalties thereon.

CROSS-REFERENCE TO RELATED PATENT APPLICATIONS

This patent application is co-pending with one related patent application entitled "METHOD AND SYSTEM FOR HEATING AND HUMIDIFYING A BREATHABLE GAS", Ser. No. 09/448,405, filed Nov. 22, 1999, and owned by the same assignee as this patent application.

FIELD OF THE INVENTION

The invention relates generally to simulated human activities, and more particularly to a method and system for simulating the metabolic consumption of oxygen in a breathable gas supplied by, for example, a semi-closed or closed circuit breathing apparatus.

BACKGROUND OF THE INVENTION

Semi-closed and closed circuit breathing apparatus are used in a variety of hazardous professions such as deep-sea diving, fire fighting and hazardous material handling, just to name a few. In each application, the breathing apparatus must be designed to provide breathable gas in extreme environmental conditions that can vary significantly during times that the breathing apparatus is required. For example, a deep-sea diver's work capacity is severely limited by the physiological effects of high surrounding pressures and chilling seawater temperatures. Specifically, increased gas density has been shown to restrict the diver's ability to do useful work by limiting the maximum voluntarily ventilation in his lungs by up to 50% when in dry chamber environments at 1000 feet of seawater (FSW). The diver's ability to breathe using an underwater breathing apparatus (UBA) at elevated pressures is also restricted due to the inherent resistance of the UBA to the dense gas medium. Water temperatures as low as −2° C. necessitate reliable systems to protect divers from excessive heat losses through their clothing and during respiration.

An equally important concern to divers is the increasingly tight control that must be maintained on the quality and composition of their breathing gas as depth increases. The very gas that we depend on to sustain life on the surface becomes toxic to the deep-sea diver. For example, nitrogen in air becomes increasingly narcotic as depth increases, causing a rapid drop in performance and judgement. Air is generally replaced with a less narcotic helium-oxygen (heliox), or hydrogen-oxygen (hydrox), mixture when the partial pressure of nitrogen ($P_{N2}$) exceeds 81.5 psi (5.55 atmospheres), equivalent to a $P_{N2}$ when breathing air at depths beyond 190 FSW (~58 meters).

In addition to the above-noted concerns, the nature of the human body must also be considered. For example, the human respiratory system contains an elegant set of defense mechanisms to protect the lungs from losing excessive heat when breathing cold, dry gases. The human respiratory tract with its intricate mucosal membrane filters foreign matter and bacteria from inhaled gases on their journey to the lungs. Additionally, the upper respiratory tract regulates the temperature and moisture content of the inhaled gases. In this way, the delicate gas exchange membranes in the lungs are protected from thermal injury and drying.

During inhalation, heat and moisture are added to the respiratory gases as they make their way from the nasal or oral passages to the alveoli. This heat is taken from a moving mucus blanket covering the upper respiratory tract (nose to the trachea). Past research has found that the temperature of inhaled air reaches 34° C. while its relative humidity reaches 80% before the air reaches the pharynx during respiration at surface conditions. By the time the air passes the trachea, the air generally reaches full body temperature and 100% relative humidity. During normal respiration of room air at 25° C. and 50% relative humidity, these heat and moisture demands on the nasal respiratory tract are relatively small, as they account for only 10–20% of the total body losses under resting conditions.

However, demand for heat and water vapor by a diver's airways increase substantially due to the effects of breathing dry, cold, dense gases at increased respiratory rates. At shallow depths, these heating demands are still relatively minor. Although drying of the airways due to gas humidification can be uncomfortable resulting in the notorious "cotton mouth" and dehydration during long dives. At depths greater than approximately 190 feet, helium makes up a large percentage of the respired gas. Helium, having a specific heat approximately five times that of air, requires a larger addition of heat to bring the inhaled gas up to body temperature. The combination of this high heat capacity and increased gas densities as the diver goes deeper results in respiratory heat losses for divers that are an appreciable part of the total body heat loss. This heat loss can even exceed the total metabolic heat production of the diver. Eventually, if unchecked, the diver's respiratory tract responds to these excessive heat demands with copious secretions that threaten the diver's life.

Obviously, it is apparent from the foregoing that breathing apparatus designs must be tested to determine their ability to address the various concerns of a particular application. Since it is not always practical or desirable to place personnel in dangerous conditions when testing a new breathing apparatus design, unmanned testing is used. Currently, such unmanned testing of closed circuit breathing apparatus involves the extraction of oxygen-rich breathing gas from the breathing apparatus and the replacement thereof with an inert gas. However, this approach does not provide test personnel with an understanding of how a human user would process the breathing gas as breathing apparatus conditions or environmental conditions are changed.

SUMMARY OF THE INVENTION

Accordingly, it is an object of the present invention to provide a method and system for simulating the human breathing process and its by products.

Still another object of the present invention is to provide a method and system for simulating human metabolic consumption of oxygen supplied by a breathing apparatus.

A further object of the present invention is to provide a method and system for simulating human metabolic consumption of oxygen contained in a breathable gas supplied by a breathing apparatus and to simulate the byproducts generated during the breathing process.

Other objects and advantages of the present invention will become more obvious hereinafter in the specification and drawings.

In accordance with the present invention, a method and system are provided that simulate the metabolic consumption of oxygen contained in a breathable gas. A variable volume chamber cyclically increases in volume to receive the breathable gas and then cyclically decreases in volume to expel an exhaust gas. A source of hydrogen gas and carbon dioxide gas is coupled to the chamber. The hydrogen gas and carbon dioxide gas are introduced into the chamber to mix with the breathable gas thereby forming the exhaust gas which includes hydrogen and oxygen. Specifically, the hydrogen gas is introduced in an amount sufficient to react with an amount of the oxygen in the exhaust gas equivalent to that used by a human during a selected level of activity. The carbon dioxide gas is introduced in an amount equivalent to that provided by a metabolic respiratory quotient associated with the same level of activity. A catalyst is coupled to the chamber to receive the exhaust gas and cause a reaction between the hydrogen and oxygen in the exhaust gas that generates simulated human exhalation to include warm water vapor and carbon dioxide.

DETAILED DESCRIPTION OF THE INVENTION

Figure 1:
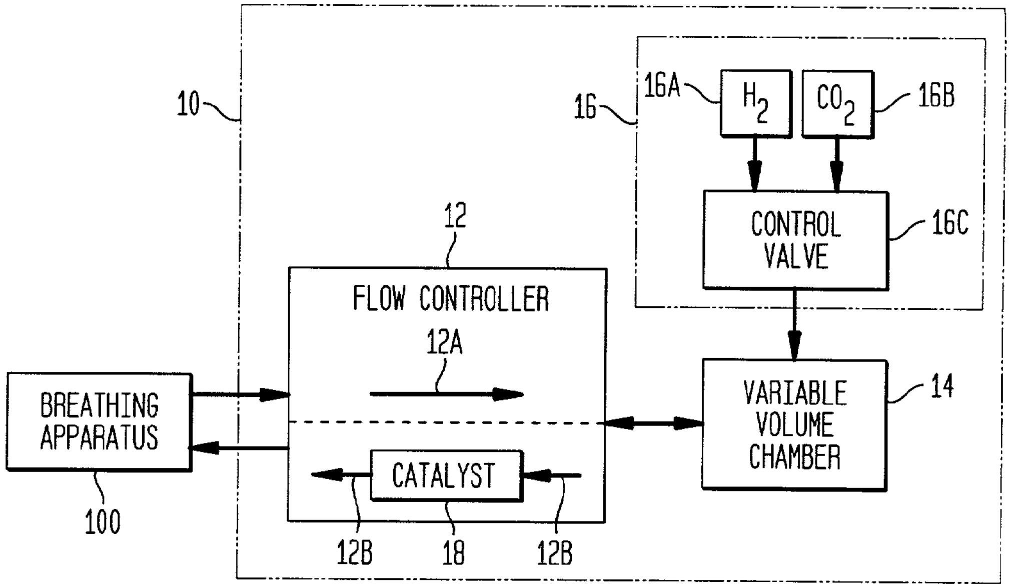
FIG. 1 is a top-level block diagram of a system for simulating human metabolic consumption of oxygen contained in a breathable gas in accordance with the present invention.

Referring now to the drawings, and more particularly to FIG. 1, a system for simulating metabolic consumption of oxygen in a breathable gas is illustrated within the box defined by dashed lines 10. By way of example, simulating system 10 will be described with respect to its use with a closed-circuit breathing apparatus 100. However, it is to be understood that simulating system 10 could also be used with an open or semi-closed circuit breathing apparatus without departing from the scope of the present invention.

Simulating system 10 includes a flow controller 12 coupled to breathing apparatus 100, a variable volume chamber 14 coupled to flow controller 12 and a source 16 of hydrogen ($H_2$) gas and carbon dioxide ($CO_2$) gas. Source 16 is representative of either individual sources 16A and 16B of hydrogen and carbon dioxide, respectively. Alternatively, the hydrogen and carbon dioxide gases could be mixed together in predetermined proportions. Source 16 also includes a control valve or metering device 16C for dispensing a controlled amount of hydrogen and carbon dioxide into chamber 14 as will be explained further below.

Variable volume chamber 14 is any device capable of cyclical increases and decreases in volume analogous to the expansion and contraction of one's lungs during the breathing process. Thus, chamber 14 increases in volume when breathable gas from breathing apparatus 100 is to be "inhaled" and then subsequently decreases in volume when exhaust gas in chamber 14 is to be "exhaled". As will be explained further below, hydrogen and carbon dioxide gas from source 16 are introduced into chamber 14 during the volume expansion thereof to create the exhaust gas that will be "exhaled" by chamber 14.

Flow controller 12 directs breathable gas from breathing apparatus 100 into chamber 14 during the chamber's volume increase phase of operation as indicated by flow path 12A.

Then, during the chamber's volume decrease phase of operation, flow controller 12 directs the exhaust gas in chamber 14 back to breathing apparatus 100 as indicated by flow path 12B. Disposed along or in flow path 12B is a catalyst 18 that will facilitate a reaction between the hydrogen and oxygen constituents in the exhaust gas traveling along path 12B. Specifically, catalyst 18 is selected to facilitate the reaction of each one mole of hydrogen with one-half mole of oxygen ($1H_2+\frac{1}{2}O_2$). This reaction produces water vapor ($H_2O$) and heat (103,968 Btu/mol $H_2$). Catalyst 18 can be any material that facilitates the above-described reaction. In tests, precious metal (e.g., palladium, platinum, etc.) catalysts have performed well. While the catalyst could make use of these precious metals in their pure form, cost considerations will generally dictate that the catalyst material be supported or suspended on some lesser expensive material such as carbon, alumina, ceramics, etc. For example, the catalyst material could be surface-deposited on granular or particle-sized particles of a support matrix. Successful tests of the present invention utilized 0.8% (weight percentage) palladium deposited on extruded pellets of carbon which is available commercially from Engelhard Corporation, Seneca, S.C.

The volume percentage of hydrogen gas mixed with the oxygen-containing breathable gas from breathing apparatus 100 must be sufficient to react with enough oxygen (in the breathable gas "inhaled" into chamber 14) to simulate the oxygen consumption of a human during the level of activity being simulated. Oxygen consumption levels as low as 0.05 pounds per hour (simulating rest) to as high as 0.6 pounds per hour (simulating extreme hard work) can thus be achieved. Such levels of activity and their corresponding oxygen consumption rates are well understood in the art. For most applications, the volume percentage of hydrogen gas in the exhaust gas in chamber 14 is on the order of approximately 1% or less. The amount of carbon dioxide introduced into chamber 14 during the chamber's volume increase phase of operation is set to simulate the metabolic respiratory quotient associated with the level of activity being simulated. Respiratory quotients, the ratio of metabolic carbon dioxide production to oxygen consumption, typically range between 0.7 to 1.1 with a norm of 0.85 being typically used to simulate human metabolism.

In one cycle of operation of simulating system 10, as chamber 14 enters its volume increase phase, flow controller 12 directs breathable gas into chamber 14. At the same time, source 16 introduces a prescribed amount of hydrogen and carbon dioxide gas into the breathable gas in chamber 14. As a result, an exhaust gas having hydrogen, oxygen (i.e., from the breathable gas) and carbon dioxide constituents is formed in chamber 14. This exhaust gas is expelled from chamber 14 during its volume decrease phase. The exhaust gas, following flow path 12B, reacts with catalyst 18 such that the gas returned to breathing apparatus 100 has: i) reduced levels of oxygen (as compared to the breathable gas provided by breathing apparatus 100) to thereby simulate the metabolic consumption of oxygen associated with a specific level of activity, ii) an amount of carbon dioxide therein commensurate with what would be produced by a human performing at the same level of activity, iii) water vapor contained therein to simulate the humidification of the breathable gas as it passes through the lungs, and iv) heat added thereto to simulate heat transfer from the airways as the gas passes through the lungs. Note that catalyst 18 does not react with the carbon dioxide passed therethrough. As a result, the gas passed to breathing apparatus 100 from flow controller 12 simulates human exhalation.

Figure 2:
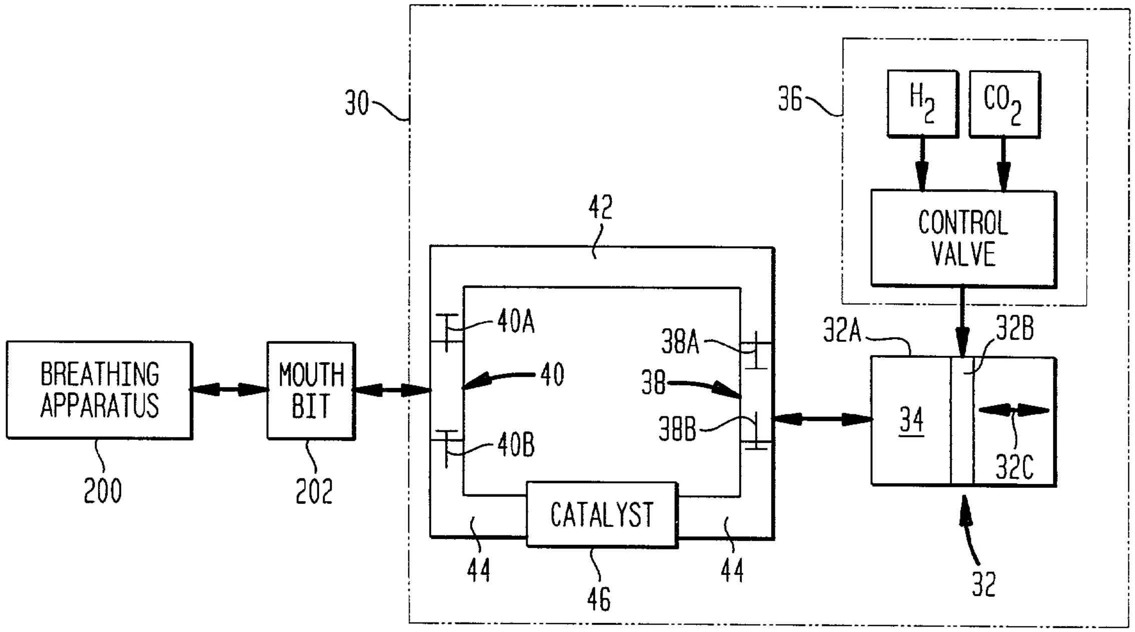
FIG. 2 is a schematic diagram of one embodiment of the present invention for use with a closed-circuit breathing apparatus.

While simulating system 10 can be implemented in a variety of ways, an embodiment thereof is illustrated in FIG. 2 as it would be coupled to a mouth bit 202 of a closed-circuit breathing apparatus 200 or a re-breather as it is sometimes called. Simulating system 30 includes a piston/cylinder assembly 32 that is operated in a cyclic fashion to create a chamber 34 that cyclically increases and decreases in volume. Assembly 32 includes a cylinder 32A with a piston 32B slidably mounted therein. A drive mechanism (not shown) is coupled to piston 32B to move same back and forth in cylinder 32A as indicated by two-headed arrow 32C. Source 36 provides hydrogen and carbon dioxide gas to chamber 34 in an analogous fashion to that described above with respect to source 16 and, therefore, requires no further description.

Mouth bit 202 is coupled to chamber 34 by first and second control valves 38 and 40, respectively. Each of valves 38 and 40 is defined by check valves 38A/38B and 40A/40B, respectively. One flow path 42 couples check valves 38A and 40A. A second flow path 44 couples check valves 38B and 40B with a catalyst 46 disposed therealong. Catalyst 46 is analogous to catalyst 18 and, therefore, requires no further description.

In one cycle of operation of system 30, piston/cylinder assembly 32 is operated to increase the volume of chamber 34. As a result, a vacuum is created in chamber 34 which opens check valves 38A and 40A (as shown) while simultaneously closing check valves 38B and 40B. During this mode of operation, breathable gas from breathing apparatus 200 is drawn through mouth bit 202 to essentially simulate user inhalation. Source 36 simultaneously supplies hydrogen and carbon dioxide gas to chamber 34 to form an exhaust gas mixture. Next, piston/cylinder assembly 32 is operated as a pump to simulate exhalation. During this mode of operation, the formed exhaust gas is pumped into valve 38 thereby closing check valve 38A and opening check valves 38B and 40B. As a result, the exhaust gas is directed through or past catalyst 46 so that, owing to the ensuing reaction between the oxygen and hydrogen constituents, a simulated human exhalation mixture is returned to mouth bit 202.

The advantages of the present invention are numerous. Metabolic consumption of oxygen as well as breathing process byproducts are produced in a simple fashion so that various breathing apparatus designs can be tested in an unmanned mode. The system can be adapted to simulate a variety of user activity levels simply by adjusting the injected amounts of hydrogen and carbon dioxide gas. Further, the present invention can be used in either open, semi-closed or closed circuit breathing systems.

Although the invention has been described relative to a specific embodiment thereof, there are numerous variations and modifications that will be readily apparent to those skilled in the art in light of the above teachings. It is therefore to be understood that, within the scope of the appended claims, the invention may be practiced other than as specifically described.

What is claimed as new and desired to be secured by Letters Patent of the United States is:

1. A system for simulating the metabolic consumption of oxygen contained in a breathable gas, comprising:

a variable volume chamber that cyclically increases in volume to receive said breathable gas and then cyclically decreases in volume to expel an exhaust gas;

a source of hydrogen gas coupled to said chamber;

a source of carbon dioxide gas coupled to said chamber;

means for introducing said hydrogen gas and said carbon dioxide gas into said chamber to mix with said breathable gas thereby forming said exhaust gas, wherein said exhaust gas includes hydrogen and oxygen, wherein said hydrogen gas is introduced in an amount sufficient to react with an amount of said oxygen in said exhaust gas equivalent to that used by a human during a selected level of activity, and wherein said carbon dioxide gas is introduced in an amount equivalent to that provided by a metabolic respiratory quotient associated with said level of activity; and a catalyst coupled to said chamber for receiving said exhaust gas, said catalyst causing a reaction between said hydrogen and said oxygen in said exhaust gas wherein simulated human exhalation is generated.

2. A system as in claim 1 wherein said source of said hydrogen gas and said source of said carbon dioxide gas comprise a single source of a mixture of said hydrogen gas and said carbon dioxide gas.

3. A system as in claim 1 wherein a volume percentage of said hydrogen gas in said exhaust gas comprises less than approximately one percent.

4. A system as in claim 1 wherein said catalyst is a precious metal.

5. A system as in claim 4 wherein said precious metal is selected from the group consisting of palladium and platinum.

6. A system for simulating the metabolic consumption of oxygen contained in a breathable gas supplied by a breathing apparatus, said system comprising:

a variable volume chamber that is operated cyclically wherein said chamber is operating in one of a vacuum mode to increase volume of said chamber and a pump mode to decrease volume of said chamber;

valve means coupled between said breathing apparatus and said chamber for defining a first flow path therethrough during said vacuum mode, said first flow path allowing said breathable gas to be drawn into said chamber;

a source of hydrogen gas coupled to said chamber;

a source of carbon dioxide gas coupled to said chamber;

means for introducing said hydrogen gas and said carbon dioxide gas into said chamber to mix with said breathable gas during said vacuum mode to form an exhaust gas, wherein said exhaust gas includes hydrogen and oxygen, wherein said hydrogen gas is introduced in an amount sufficient to react with an amount of said oxygen in said exhaust gas equivalent to that used by a human during a selected level of activity, and wherein said carbon dioxide gas is introduced in an amount equivalent to that provided by a metabolic respiratory quotient associated with said level of activity;

said valve means defining a second flow path therethrough during said pump mode, said second flow path allowing said exhaust gas to be expelled from said chamber; and a catalyst coupled to said valve means for receiving said exhaust gas during said pump mode, said catalyst causing a reaction between said hydrogen and said oxygen in said exhaust gas wherein simulated human exhalation is generated.

7. A system as in claim 6 wherein said breathing apparatus is a closed circuit breathing apparatus, said valve means coupling said catalyst to said breathing apparatus, wherein said second flow path directs said simulated human exhalation to said breathing apparatus during said pump mode.

8. A system as in claim 6 wherein said variable volume chamber comprises a piston/cylinder assembly, and wherein said pump mode occurs during a power stroke of said piston/cylinder assembly and said vacuum mode occurs during a return-to-battery stroke of said piston/cylinder assembly.

9. A system as in claim 6 wherein said source of said hydrogen gas and said source of said carbon dioxide gas comprise a single source of a mixture of said hydrogen gas and said carbon dioxide gas.

10. A system as in claim 6 wherein a volume percentage of said hydrogen gas in said exhaust gas comprises less than approximately one percent.

11. A system as in claim 6 wherein said catalyst is a precious metal.

12. A system as in claim 11 wherein said precious metal is selected from the group consisting of palladium and platinum.

13. A method of simulating the metabolic consumption of oxygen contained in a breathable gas supplied by a breathing apparatus, said method comprising the steps of:

providing a variable volume chamber capable of cyclic operation in one of a vacuum mode to increase volume of said chamber and a pump mode to decrease volume of said chamber;

directing said breathable gas into said chamber during said vacuum mode;

introducing hydrogen gas and carbon dioxide gas into said chamber to mix with said breathable gas during said vacuum mode to form an exhaust gas, wherein said exhaust gas includes hydrogen and oxygen, wherein said hydrogen gas is introduced in an amount sufficient to react with an amount of said oxygen in said exhaust gas equivalent to that used by a human during a selected level of activity, and wherein said carbon dioxide gas is introduced in an amount equivalent to that provided by a metabolic respiratory quotient associated with said level of activity;

providing a catalyst capable of causing a reaction between said hydrogen and said oxygen in said exhaust gas; and directing said exhaust gas from said chamber to said catalyst during said pump mode wherein simulated human exhalation is generated.

14. A method according to claim 13 wherein said breathing apparatus is a closed circuit breathing apparatus, said method further comprising the step of directing said simulated human exhalation to said breathing apparatus during said pump mode.

15. A method according to claim 13 wherein said step of introducing comprises the step of separately introducing said hydrogen gas and said carbon dioxide gas into said chamber.

16. A method according to claim 13 further comprising the step of mixing said hydrogen gas with said carbon dioxide gas prior to said step of introducing.

17. A method according to claim 13 wherein said step of introducing includes the step of maintaining a volume percentage of said hydrogen gas in said exhaust gas that is less than approximately one percent.

18. A method according to claim 13 wherein said reaction produces heat and water vapor.

* * * * *